United States Patent
Mercier et al.

(10) Patent No.: US 9,456,555 B2
(45) Date of Patent: Oct. 4, 2016

(54) AGENT FOR TREATING GRAPE VINE WOOD

(75) Inventors: Miguel Mercier, Vix (FR); Olivier Zekri, La Rochelle (FR)

(73) Assignee: Financiere Mercier, Vix (FR)

( * ) Notice: Subject to any disclaimer, the term of this patent is extended or adjusted under 35 U.S.C. 154(b) by 125 days.

(21) Appl. No.: 14/233,574

(22) PCT Filed: Jul. 18, 2012

(86) PCT No.: PCT/EP2012/064061
§ 371 (c)(1),
(2), (4) Date: Jan. 17, 2014

(87) PCT Pub. No.: WO2013/011053
PCT Pub. Date: Jan. 24, 2013

(65) Prior Publication Data
US 2014/0157661 A1    Jun. 12, 2014

(30) Foreign Application Priority Data
Jul. 18, 2011    (FR) .................... 11 56522

(51) Int. Cl.
*A01N 59/08* (2006.01)
*A01G 1/06* (2006.01)
*A01N 59/00* (2006.01)

(52) U.S. Cl.
CPC ................ *A01G 1/06* (2013.01); *A01N 59/00* (2013.01); *A01N 59/08* (2013.01)

(58) Field of Classification Search
CPC .. A01N 59/00; A01N 59/08; A01N 2300/00; A01G 1/06
See application file for complete search history.

(56) References Cited

U.S. PATENT DOCUMENTS

| | | | | |
|---|---|---|---|---|
| 4,937,971 A | * | 7/1990 | Collas | A01G 1/06 47/58.1 R |
| 2011/0059185 A1 | | 3/2011 | Saefkow et al. | |

FOREIGN PATENT DOCUMENTS

| | | | |
|---|---|---|---|
| EP | 0347731 A2 | | 12/1989 |
| RU | 2170499 | * | 7/2001 |
| RU | 2263432 | * | 11/2005 |
| WO | WO-01/58265 A2 | | 8/2001 |
| WO | WO-2009106645 A2 | | 9/2009 |

OTHER PUBLICATIONS

Tome et al. Science of the Total Environment, 2008, 393, 351-357.*
Kharchenko et al., RU 2263432, English Machine Translation obtained on Sep. 20, 2015.*
Bolotov et al., RU 2170499, English Machine Translation obtained on Sep. 20, 2015.*
International Search Report for PCT/EP2012/064061 mailed Aug. 29, 2012.
English translation (machine translation) of EP-0347731-A2 published Dec. 27, 1989.
Les Maladies du Bois de la Vigne [Diseases of Grapevine Wood], Nov. 16-17, 2010, Villefranche/Saone [France], Compte Rendu, edited by Philippe Larignon, IFV (Institute Francais de la Vigne et du Vin—French Grapevine and Wine Institute), pp. 1-59.
English translation of Bernos, Laurent, Recherche et évaluation de procédés permettent la production de plants indemnes de champignons associés aux maladies du bois (programme CASDAR) ("Research and evaluation processes for the production of free plants associated with fungi diseases of wood (CASDAR program"), pp. 27-29 of the document, 2010.
English translation of Vigues, Virginie et al., "Les maladies du bois Tests de méthods de désinfection en pépinière" (Wood diseases Testing methods of disinfection in the nursery), pp. 31-33 of the document, 2010.

* cited by examiner

*Primary Examiner* — Ali Soroush
*Assistant Examiner* — Genevieve S Alley
(74) *Attorney, Agent, or Firm* — Polsinelli PC

(57) ABSTRACT

The invention relates to the use of neutral anolyte for decontaminating grape vine wood.

17 Claims, No Drawings

AGENT FOR TREATING GRAPE VINE WOOD

RELATED APPLICATIONS

This application is a national stage application (under 35 U.S.C. §371) of PCT/EP2012/064061, filed Jul. 18, 2012, which claims priority of French application 1156522, filed on Jul. 18, 2011.

The invention relates to a method of producing grapevine seedlings comprising various steps of cleaning and disinfecting grapevine wood.

Diseases of the wood (eutypiose, esca and BDA), long regarded as secondary, are now an increasing preoccupation of viticulturists. In the absence of means of preventive or therapeutic control, recommended prophylactic measures are followed very unevenly.

Studies conducted in the nursery have shown that certain fungi responsible for the three main fungal diseases of grapevine wilting, namely eutypiose (*Eutypa lata*), esca (*Phaeomoniella chlamydospora, Phaeoacremonium aleophilum, Fomitiporia mediterranea* and *E. lata* being implicated) and Black Dead Arm (*Botryosphaeria obtusa, Botryosphaeria dothidea parva* and *stevensii*) are present during the stages of production of the seedlings. Laurent BERNOS states that "some [of these steps] have been identified, such as rehydration, stratification (for *Phaeomoniella chlamydospora* and certain *Botryosphaeriaceae*) and growing in the field (for *Phaeoacremonium aleophilum, Phomopsis viticola* and certain *Botryosphaeriaceae*). To date, there is no effective means of disinfection whatever the stage of production of the seedlings. Only treatment with hot water, used for combating golden flavescence, shows partial efficacy on some of these fungi" (see *Research and evaluation of methods for producing seedlings unaffected by fungi associated with diseases of the wood* (*Casdar programme*) in Les Maladies du Bois de la Vigne [Diseases of Grapevine Wood], 16-17 Nov. 2010, Villefranche/Saone Compte Rendu, edited by Philippe Larignon, IFV (Institut Francais de la Vigne et du Vin—French Grapevine and Wine Institute), http://www.vignevin-sudouest.com/publications/fiches-pratiques/documents/MDB-2010_000.pdf).

In particular, EP 347731 describes the use of hydrogen peroxide or of ozone for treating vines against parasites ([0005]). In no case does it suggest or propose substituting the neutral anolyte in these products.

WO 2009/106645 describes a method of cleaning food-processing plants using an aqueous solution containing a particular anolyte, and so does not relate to the decontamination of grapevine wood.

WO 01/58265 envisages the use of chlorine dioxide for controlling parasites present in soils (such as insects and nematodes).

It is all the more important to ensure that grapevine seedlings obtained from nurseries are as free as possible from germs of these fungi, as there is currently no effective method of chemical or biological control in the vineyard, sodium arsenite no longer being approved, as it is too toxic to humans and the environment. It should be noted that the combination of carbendazim and fluzilazole has provisional approval against esca, and is applied by painting the wound immediately after pruning.

In the field for the grapevine, the best method of combating these pathogens is prophylaxis, and notably the removal of dead wood, or applying tar or mastic on the wounds very quickly after pruning.

The applicants have shown that neutral anolyte can be used for decontaminating grapevine wood, notably during production of grapevine seedlings in the nursery, and that this product can give very positive results with respect to the presence of pathogenic fungi.

The neutral anolyte can also be used for decontaminating and disinfecting all tools and equipment used in the production of grapevine seedlings.

Starting from a mixture of water and salt, using a technique of membrane electrolysis, units produce a biocide called neutral anolyte. This solution has a very strong disinfecting power (bactericidal, virucidal, fungicidal, algicidal). Its oxidizing power also acts on the biofilm in pipelines. Moreover, the neutral anolyte activates water. In the system for production of the disinfectant, an electric current circulates in a salt-saturated solution between two metallic elements, called anode and cathode. The brine produced dissociates, generating 2 products: the acid anolyte: pH between 2 and 5 and the catholyte: pH between 11 and 13. These 2 solutions are mixed in the storage tank. The final product, called neutral anolyte, is characterized by a neutral pH and a redox potential above 750 mV (that of chlorinated water is 400 mV).

The neutral anolyte is thus already known as a disinfectant and is used in various areas of agriculture, notably for disinfection in livestock farming. Thus, in the areas of agriculture and horticulture, this product has been described as being suitable for use for disinfection in the storage of grain and seeds or purification of irrigation water for spraying cereal crops, so as to reduce parasites. It can also protect silage against contamination.

The concentration of neutral anolyte can be modified, by mixing with water. Thus, a composition is obtained with a 10% (by volume) concentration of neutral anolyte by mixing nine volumes of water with one volume of neutral anolyte. If no water is added, the solution is therefore of 100% concentration.

However, this product has never been used or proposed for production of grapevine seedlings, which are "woods", and whose pathogens are located both on the inside and on the outside. Thus, this product succeeds in having an effect on the bark, but also in the vascular tissues.

It should thus be noted that Vigues et al. (*Diseases of wood, Tests on methods of disinfection in the nursery* in the Report of the conference on diseases of grapevine wood on Nov. 16 and 17, 2010, op. cit.) do not mention the neutral anolyte in the products envisaged for disinfecting grapevine seedlings, although several possible disinfectants were tested.

Moreover, the applicants have shown that application of the neutral anolyte can preserve favorable fungi (such as the *Trichoderma*, which are effective against certain pathogens) introduced during production of the seedlings.

The invention thus relates to the use of neutral anolyte for decontaminating grapevine wood. This use is notably carried out in the nursery during the production of grapevine seedlings, but can also be carried out in the open.

The invention also relates to a method for producing grapevine seedlings comprising at least one step of contacting rootstock, scions or grapevine seedlings (obtained after grafting) with neutral anolyte.

Like all plants, the grapevine can be propagated by sowing, taking cuttings or grafting. In actual fact, the need for grafting on the vast majority of soils has encouraged nurserymen to unify the process.

The rootstock cuttings are taken during the vegetative period (winter) at a length of about 30 cm, those of the scions at a few cm, at the time of pruning.

The cuttings are "cleaned", sorted, and stored at low temperature, in an environment saturated with humidity.

For making the seedlings, the rootstock is brought to the desired length, and then dipped in a disinfecting solution. The scions are cut up and rehydrated.

They are then assembled using a notch. There are several forms of notch. In all cases it must permit good development of the graft union callus, and be sufficiently firm to withstand subsequent manipulation. Generally an omega graft is used, which does not require tying and allows a very fast grafting rate.

Generally and in order to prevent contamination and protect the graft union, the unions are dipped in a sterilizing wax that is impervious to air, in order to consolidate the graft and prevent drying of the tissues. The assemblies (paraffin-treated scions) are then left to heal horizontally in containers filled with wet sand or some other mineral (such as vermiculite) in a stove. These containers (wooden boxes) are made impervious with plastic film. This operation allows formation of the graft union callus in just a few days.

After healing, the water is emptied from the boxes and they are placed in a warm room between 25° C. and 28° C. and with hygrometry from 70 to 80%. To prevent drying of the scions, a film and chips of wood or some other element (vermiculite) are put on the boxes.

Holding in the warm room triggers stratification: the graft union callus gets larger, and the buds and rootlets develop.

The goal of stratification or forcing is thus to obtain a graft union tissue that produces a thickening between the scion and the rootstock, to prepare the heel of the rootstock for putting out future roots, and to cause development of the shoot of the scion with the first two or three small leaves.

The successfully grafted seedlings are then planted in the nursery or in the open (in the fields), generally from May to November/December, to develop a good root system on the heel of the rootstock and obtain a shoot on the scion.

The seedlings ready to be sold are then dug up, sorted, packed and stored in a cold room until delivery.

In one embodiment of the method according to the invention, it has a step of application of neutral anolyte on the rootstock and scions during the rehydration phase preceding the grafting step.

For said application, it is preferable for the neutral anolyte to have a concentration between 3 and 50% (by volume), preferably between 3 and 30%, more preferably between 3 and 10%. Selection of the concentration is determined according to the origin and initial state of the plant material taken. In fact, if there is a high risk of contamination of the rootstock and scions, a composition with a higher concentration of neutral anolyte will be used.

In this embodiment, application is preferably carried out by total immersion of the plant material in the solution of neutral anolyte for a duration of between 10 and 48 hours, preferably between 10 and 24 hours, more preferably between 10 and 15 hours. The duration of application mainly depends on the state of dehydration of the wood.

In a preferred embodiment, the plant material is immersed in a solution of neutral anolyte with 6% concentration for 12 h.

It is preferable to renew the disinfectant solution between each bath, so as to guarantee that the disinfectant capacity is maintained. However, this solution can also be kept for 2 or 3 applications.

In one embodiment of the method according to the invention, it comprises a step of application of neutral anolyte on grapevine seedlings after grafting, during the healing phase.

This application is carried out during storage of the assemblies in the containers, and preferably by hydration of the sand or other minerals used with a solution of neutral anolyte at a concentration above 80%, preferably equal to 100%.

In one embodiment of the method according to the invention, it comprises a step of application of neutral anolyte on the grapevine seedlings during the stratification phase.

In this method of application, the neutral anolyte is preferably used at a concentration between 3 and 10%. It is applied by spraying on the buds in the opening phase. Moreover, the solution of neutral anolyte at this concentration is used in the bulk bins, on the heel.

This step is applied starting from the moment when the top covering of vermiculite is removed and the seedlings are kept in a warm room, at a temperature between 25 and 29° C., preferably around 28-29° C. with water at the level of the heel (5 cm of water in the boxes). The frequency of spraying is variable and is applied in such a way as to keep the environment at high humidity (70 to 80% humidity) (thus, generally several sprayings are carried out per day).

The method can also have a step of application of neutral anolyte on the grapevine seedlings during the growth phase, after planting them, in the nursery or in the open.

For this application, neutral anolyte is preferably used at a concentration of up to 50%, preferably between 15 and 50%. Application is carried out by spraying on the leaves and/or dropwise during irrigation of the seedlings.

The neutral anolyte is used starting from the 4-leaf stage. When the plants have rooted in the open, application is preferably repeated about every 7 days in a wet period and every 14 days in a dry period.

Finally, the neutral anolyte can also be used for preparing the grafted seedlings before packing and storing in a cold room during preparation for delivery.

This application is carried out on the grafted rooted seedlings by immersing the bare roots in a solution of neutral anolyte at a concentration above 75%, preferably equal to 100%, for a time preferably between 1 and 5 hours. This last treatment can be repeated before delivery of the seedlings if the storage time exceeds 2 months.

Moreover, it is particularly beneficial to disinfect all equipment and elements likely to come in contact with the plant material by using a solution of neutral anolyte at a concentration above 75%, preferably equal to 100%. This disinfection is preferably carried out at least once daily.

In another embodiment, the neutral anolyte is used on rooted vines in the open. In this embodiment, the neutral anolyte is used as an aid for combating or preventing fungal infections in the open. In particular, the neutral anolyte can be used when pruning vines, by spraying the wound immediately after pruning. It is preferable to use a solution of neutral anolyte at a concentration between 3 and 75%, preferably between 25 and 50%.

This use does not exclude the use of tar or mastic on pruning wounds.

The invention thus relates to a method of producing a grafted grapevine seedling comprising at least one step selected from a) a step consisting of cutting a rootstock and a scion b) a step consisting of assembling said rootstock and scion to form an assembly c) a step comprising healing of the assembly to form a graft union callus and stratification of said callus d) a step of growth of the grapevine seedling, said method being characterized in that a solution of neutral anolyte is applied on the seedlings during production in said step.

In a particular embodiment, said step is step a).
In a particular embodiment, said step is step b).
In a particular embodiment, said step is step c).
In a particular embodiment, said step is step d).

In a particular embodiment, the method comprises at least two steps in which the grapevine seedlings are exposed to the neutral anolyte during production. In a particular embodiment, the two steps in which the seedlings are exposed to the neutral anolyte are steps a) and b). In another embodiment, they are steps a) and c). In another embodiment, they are steps b) and c). In another embodiment, they are steps a) and d). In another embodiment, they are steps b) and d). In another embodiment, they are steps c) and d).

In a particular embodiment, the method comprises at least three steps in which the grapevine seedlings are exposed to the neutral anolyte during production. In a particular embodiment, the three steps in which the seedlings are exposed to the neutral anolyte are steps a), b) and c). In another embodiment, they are steps a), b) and d). In another embodiment, they are steps a), c) and d). In another embodiment, they are steps b), c) and d).

In a particular embodiment, the method comprises the four steps a) to d) and the grapevine seedlings are exposed during production to the neutral anolyte in four steps a) to d). The conditions of application of the neutral anolyte are preferably those described above.

The present invention therefore discloses neutral anolyte as agent for decontaminating grapevine wood, both as prophylactic agent (prevention) notably during the preparation of grapevine seedlings, and as therapeutic agent.

The use of neutral anolyte thus allows production of healthy grapevine seedlings, free from the fungi identified as being responsible for the diseases of the wood. The method according to the invention does not claim to suppress all the commensal flora of the grapevine but to significantly reduce the proportions of inoculum of the pathogenic fungi present and to prevent proliferation of the latter during the production process of the grapevine seedlings.

EXAMPLES

Example 1

Comparative In Vivo Test of the Treatment with the Neutral Anolyte with $H_2O_2$ (Hydrogen Peroxide), Desogerm (Biofungicide—A.C.I Laboratory, Denoted T1), and $H_2O$ Comparative tests "in vivo" and "in vitro" were carried out to evaluate whether water, hydrogen peroxide, desogerm and the neutral anolyte (100%) had an effect on 8 fungi referenced as pathogens and associated with various diseases of the wood.

The in vivo test consisted of evaluating a set of 1025 plants derived from 4 rootstocks and 5 different varieties (to limit the varietal effect). Samples of the seedlings were taken before and after treatment.

The treatment consisted of immersing the wood in the various solutions under test for 12 h, i.e. the usual rehydration time of the wood in the nursery (overnight).

The samples of wood before and after treatment were analyzed, by extracting the total DNA of the wood samples taken, and evaluation by molecular diagnostics (PCR analysis) for the presence or absence of these 8 fungi: *Botryosphaeria obtusa*, *Botryosphaeria dothidea*, *Eutypa lata*, *Fomitiporia punctata*, *Phaeacremonium aleophilum*, *Phaeomonelia chlamydospora*, *Phaeoacremonium* spp. and *Cylindrocarpon destructans*.

The results obtained are presented in Table I.

TABLE I

Comparison of treatment for disinfection of wood in vivo
(THW: treatment with hot water)

| | With THW (50° C.-45 min) | | | | Without THW | | | |
|---|---|---|---|---|---|---|---|---|
| Variety Scions/PG | $H_2O_2$ | T1 | Neutral anolyte | H2O | $H_2O_2$ | T1 | Neutral anolyte | $H_2O$ |
| SO4(203) | B.obt | | | | B.obt | E.lata | | B.obt |
| R110 (151) | B.obt | B.obt | | | B.obt | B.obt | | B.obt |
| Sauv.B (905) | | | | | B.obt | | | B.obt |
| Merlot.N (182) | B.obt | | | | | | | B.obt |

Only 2 rootstocks and 2 varieties are shown as they are the most significant in terms of representativeness for wine production. The results indicate that the DNA of two fungi only was found in the samples.

The presence of the name of a fungus (B. obt for *Botryosphaeria obtuse*) in this table indicates that this fungus was found at least once among the individuals evaluated. If nothing is indicated, it is because it was never found.

These results show that the neutral anolyte displays good efficacy against *Botryosphaeria obtusa*. It is, however, difficult to draw conclusions about the other pathogens that were not even identified before treatment.

These results were confirmed using the technique of nephelometry: thus, the use of neutral anolyte at a concentration of 25% made it possible to inhibit the growth of the pathogens *Neofusiccum parvum* and *Diplodia seriata* (inhibition between 80 and 95%). Inhibition was 40-50% at a concentration of 6%.

Example 2

Comparative Test In Vitro of the Treatment With Neutral Anolyte with $H_2O_2$ (Hydrogen Peroxide), Desogerm (Biofungicide—A.C.I Laboratory, Denoted T1), and $H_2O$ That is why an in vitro test was carried out, in order to compare the effect of water, hydrogen peroxide, desogerm and the neutral anolyte (100%) on 8 fungi referenced as pathogens and associated with various diseases of the wood.

Strains of the 8 fungi mentioned above were deposited on culture medium with low discrimination (PDA—Potato Dextrose Agar—Medium).

Then 10 ml of each solution was added to Petri dishes with the inoculated strains of fungi, and left for 12 h. After this period, the 10 ml was poured off and the growth of the fungi was observed for several weeks, measuring the radius of mycelium that had or had not formed as the fungi grew, at a temperature of about 25° C.

These in vitro experiments demonstrated absence of growth for all the fungi put in contact with the neutral anolyte, which was not the case for the other solutions tested.

It may, however, be noted that hydrogenated water displays a certain efficacy in inhibition of the growth of the fungi.

Example 3

Percentage of Recovery after Planting, Comparative Test In Vivo of the Treatment with the Neutral Anolyte with $H_2O_2$ (Hydrogen Peroxide), Desogerm (Biofungicide—A.C.I Laboratory, Denoted T1), and $H_2O$ The result of recovery (take) after planting (growth of the plants) is very important, as the treatment must not be injurious for the grapevine seedlings.

The percentage take was evaluated on more than 500 seedlings and the percentage of recovery (take) is as shown in Table II.

TABLE II

Percentage of recovery of the treated seedlings after different treatments

| | Neutral anolyte | T1 | $H_2O_2$ | Control $H_2O$ |
|---|---|---|---|---|
| 8 days after planting | 74.5% | 74.7% | 59% | 79.4% |
| 20 days after planting | 95.9% | 94.9% | 94.8% | 95% |

It can be seen that hydrogen peroxide alters the wood when it is put in contact with the cuttings during the rehydration phase. The neutral anolyte provides similar or even better results in terms of disinfection without altering the wood. The physiological integrity of the plant is still the most important element to take into account when producing a grapevine seedling. Consequently, hydrogen peroxide is less beneficial than the neutral anolyte as disinfectant against grapevine pathogens.

Example 4

Maintaining the Presence of Favorable Fungi

During the production of grapevine seedlings, it is possible to inoculate them with *Trichoderma atroviride*, which has an effect against the fungi responsible for the diseases of grapevine wood. The seedlings were inoculated with *Trichoderma* by immersion in several places and at several points of time in a solution of *Trichoderma* at a concentration of $10^7$ spores/ml.

The evaluations on the seedlings inoculated with *Trichoderma* were carried out following the same type of protocol as in example 1, i.e. by immersion of grapevine seedlings ready to be marketed for 12 h in neutral anolyte at 100%.

The evaluation was first carried out visually by observation, in the Petri dish, of the growth of the fungus from disks of wood taken from the samples of seedlings tested, then by molecular identification by PCR to validate the precise identity of the strain of *Trichoderma* growing.

All the dishes seeded with disks of wood obtained from seedlings with *Trichoderma* and then immersed in the 100% neutral anolyte for 12 h revealed the presence of *Trichoderma* in the dish and by PCR analysis.

This demonstrates that this *Trichoderma* is not sufficiently affected by the neutral anolyte to disappear. Inhibition is only 12% at a concentration of neutral anolyte of 6%, and 54% for a concentration of 25%, as measured by nephelometry.

Example 5

Other Protocol

The system can be perfected using concentrations of neutral anolyte adapted to the physiological stage of the plant.

Indeed, application of neutral anolyte at 100% for 12 h may prove injurious to the wood, despite the positive results for recovery.

The doses and application times were reduced, but the neutral anolyte is applied at several points of time.

a step of application of neutral anolyte on the rootstocks and scions during the rehydration phase preceding the grafting step.

Thus, neutral anolyte is applied at a concentration between 3 and 50% (depending on the origin and the initial state of the plant material taken) on the rootstocks and scions after collection and storage of the wood, during the rehydration phase preceding the grafting step. Application is carried out by total immersion of the plant material in the solution for a time that can range from 12 to 48 hours depending on the state of dehydration.

The grapevine seedlings are also exposed to the neutral anolyte during the steps of healing (concentration 100%) and stratification (concentration 3 to 10%) after grafting.

The neutral anolyte is also applied at a concentration that can be up to 50% on the grapevine seedlings during the growth phase.

This protocol also gives positive results, since nearly all the seedlings produced (98 out of 100 tested) are free from any fungus within the limits of the diagnostic tools.

Example 6

Tests in the Open

The results for application in the open at an established vineyard are also very encouraging, despite a year relatively preserved in terms of fungal pressure of the mildew or oidium type.

Thus, the plot that only received neutral anolyte at 50%, once weekly, as phytosanitary treatment, does not show any sign of fungal contamination.

The invention claimed is:

1. A method for decontaminating grapevine wood or seedling, wherein the seedlings are grafted grapevine seedlings, wherein said method comprises the step of applying neutral anolyte on said grapevine wood or seedling, thereby obtaining disinfected grapevine wood or seedling, wherein said method is performed during the process of production of grapevine seedlings, and the process of production of grapevine seedlings comprises
    grafting rootstocks and scions to form grafted grapevine seedlings;
    healing the grafted grapevine seedlings;
    stratifying the grafted grapevine seedlings; and
    growing the grafted grapevine seedlings.

2. The method of claim 1, wherein said process of production further comprises rehydrating said rootstocks and scions, and applying neutral anolyte on the rootstocks and scions during rehydration, preceding the grafting step.

3. The method of claim 2, wherein neutral anolyte is applied at a concentration between 3 and 50% (by volume).

4. The method of claim 2, wherein said application is carried out by total immersion of the rootstocks and scions in a solution of neutral anolyte for a duration of between 10 and 48 hours.

5. The method of claim 1, wherein neutral anolyte is applied by exposing the grafted grapevine seedlings to the neutral anolyte during the healing step.

6. The method of claim 5, wherein said healing step is carried out in containers containing said grafted grapevine seedlings and sand or other minerals; and application is carried out by hydration of the sand or other minerals present in the containers during healing.

7. The method of claim 5, wherein neutral anolyte is applied at a concentration above 80%.

8. The method of claim 1, wherein neutral anolyte is applied on the grafted grapevine seedlings during the stratification step.

9. The method of claim 8, wherein neutral anolyte is applied at a concentration between 3 and 10%.

10. The method of claim 8, wherein said application is carried out by spraying on the buds in the opening phase.

11. The method of claim 1, wherein neutral anolyte is applied on the grafted grapevine seedlings during the growth step.

12. The method of claim 11, wherein neutral anolyte is applied at a concentration of up to 50%.

13. The method of claim 11, wherein neutral anolyte is applied by spraying on the leaves and/or dropwise during irrigation of the grafted grapevine seedlings.

14. The method of claim 1, wherein neutral anolyte is applied on rooted vines in the open.

15. The method of claim 14, wherein neutral anolyte is applied on the vines when pruning said vines.

16. The method of claim 14, wherein neutral anolyte is applied at a concentration above 75%.

17. The method of claim 1, wherein application of neutral anolyte inhibits growth of at least one fungus selected from the group consisting of *Botryosphaeria obtusa, Botryosphaeria dothidea, Eutypa lata, Fomitiporia punctata, Phaeacremonium aleophilum, Phaeomonelia chlamydospora, Phaeoacremonium* spp. and *Cylindrocarpon destructans* in said wood.

* * * * *